United States Patent
Krywcun et al.

(10) Patent No.: US 11,103,703 B2
(45) Date of Patent: Aug. 31, 2021

(54) COCHLEAR IMPLANTS INCLUDING ELECTRODE ARRAYS AND METHODS OF MAKING THE SAME

(71) Applicant: ADVANCED BIONICS AG, Staefa (CH)

(72) Inventors: Matt V. Krywcun, Saugus, CA (US); James George Elcoate Smith, Santa Clarita, CA (US); Uli Gommel, Valencia, CA (US); Martin Sandoval Perez, Van Nuys, CA (US)

(73) Assignee: Advanced Bionics AG, Staefa (CH)

(*) Notice: Subject to any disclaimer, the term of this patent is extended or adjusted under 35 U.S.C. 154(b) by 69 days.

(21) Appl. No.: 16/319,638

(22) PCT Filed: Aug. 11, 2016

(86) PCT No.: PCT/US2016/046621
§ 371 (c)(1),
(2) Date: Jan. 22, 2019

(87) PCT Pub. No.: WO2018/031025
PCT Pub. Date: Feb. 15, 2018

(65) Prior Publication Data
US 2020/0188666 A1    Jun. 18, 2020

(51) Int. Cl.
*A61N 1/36* (2006.01)
*A61N 1/05* (2006.01)

(52) U.S. Cl.
CPC ....... *A61N 1/36038* (2017.08); *A61N 1/0541* (2013.01)

(58) Field of Classification Search
None
See application file for complete search history.

(56) References Cited

U.S. PATENT DOCUMENTS

| | | |
|---|---|---|
| 4,686,765 A | 8/1987 | Byers et al. |
| 5,000,194 A | 3/1991 | Van Den Honert et al. |
| 5,037,497 A | 8/1991 | Stypulkowski |
| 5,123,422 A | 6/1992 | Charvin |
| 5,439,485 A | 8/1995 | Mar et al. |
| 5,534,022 A | 7/1996 | Hoffmann et al. |
| 5,542,173 A | 8/1996 | Mar et al. |
| 5,580,699 A | 12/1996 | Layman et al. |
| 5,658,709 A | 8/1997 | Layman et al. |
| 5,824,022 A | 10/1998 | Zilberman et al. |
| 6,125,302 A | 9/2000 | Kuzma |
| 6,144,883 A | 11/2000 | Kuzma |
| 6,195,586 B1 | 2/2001 | Kuzma |

(Continued)

FOREIGN PATENT DOCUMENTS

WO   WO2018/209872 A1   11/2018

OTHER PUBLICATIONS

PCT International Search and Written Opinion dated Nov. 30, 2016 for PCT App. Ser. No. PCT/US2016/046621.

(Continued)

*Primary Examiner* — Paula J Stice
(74) *Attorney, Agent, or Firm* — Henricks Slavin LLP

(57) ABSTRACT

A method of forming an electrode array includes the steps of positioning a workpiece on a mold part, compressing the workpiece into the mold part to form a contact, and introducing resilient material into the mold part to form a flexible body.

19 Claims, 10 Drawing Sheets

(56) References Cited

U.S. PATENT DOCUMENTS

| | | |
|---|---|---|
| 6,309,410 B1 | 10/2001 | Kuzma et al. |
| 6,374,143 B1 * | 4/2002 | Berrang ............... A61N 1/0541 600/379 |
| 6,421,569 B1 | 7/2002 | Treaba et al. |
| 7,451,000 B2 | 11/2008 | Gibson et al. |
| 8,461,042 B2 | 6/2013 | Dadd et al. |
| 8,620,459 B2 | 12/2013 | Gibson et al. |
| 8,782,884 B2 | 7/2014 | Capcelea et al. |
| 9,694,174 B2 | 7/2017 | Dadd et al. |
| 10,406,350 B2 | 9/2019 | Mercanzini et al. |
| 2003/0171787 A1 * | 9/2003 | Money ............... A61N 1/36038 607/57 |
| 2010/0036470 A1 | 2/2010 | Nielsen |
| 2010/0287770 A1 | 11/2010 | Dadd et al. |
| 2011/0016710 A1 | 1/2011 | Dadd et al. |
| 2011/0126410 A1 | 6/2011 | Capcelea et al. |
| 2013/0079749 A1 | 3/2013 | Overstreet et al. |
| 2013/0238074 A1 | 9/2013 | Zimmerling |
| 2014/0163662 A1 | 6/2014 | Beerling et al. |
| 2015/0032194 A1 | 1/2015 | Mergen et al. |
| 2015/0246234 A1 | 9/2015 | Hazard et al. |
| 2016/0022990 A1 * | 1/2016 | Risi ..................... A61N 1/0541 607/57 |
| 2016/0082249 A1 | 3/2016 | Thenuwara et al. |
| 2016/0193460 A1 | 7/2016 | Xu et al. |
| 2021/0106816 A1 | 4/2021 | Clabeaux et al. |
| 2021/0187282 A1 | 6/2021 | Salvatierra |

OTHER PUBLICATIONS

U.S. Appl. No. 16/319,638, filed Jan. 22, 2019, 2020/0188666 A1.
U.S. Appl. No. 16/599,102, filed Oct. 10, 2019, 2021/0106816 A1.
U.S. Appl. No. 16/724,291, filed Dec. 21, 2019.
U.S. Appl. No. 17/232,131, filed Apr. 15, 2021.

* cited by examiner

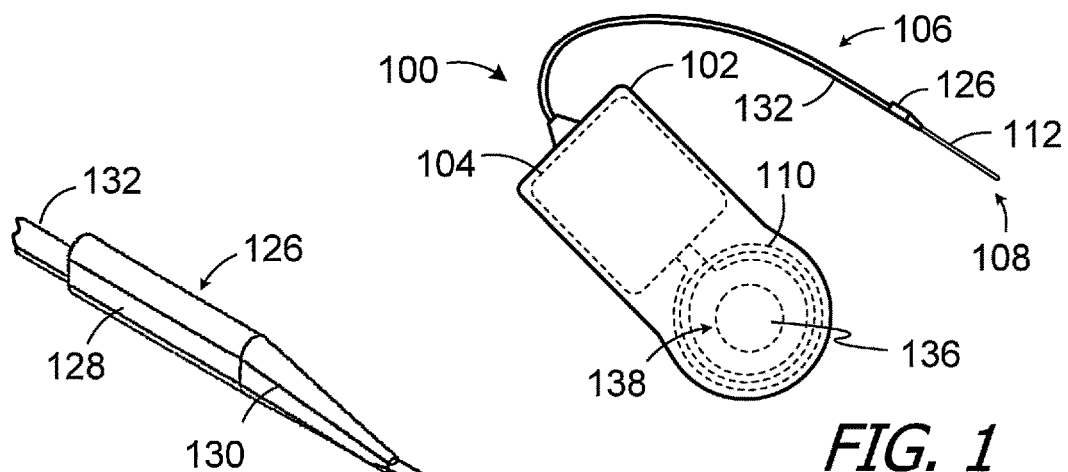
FIG. 1
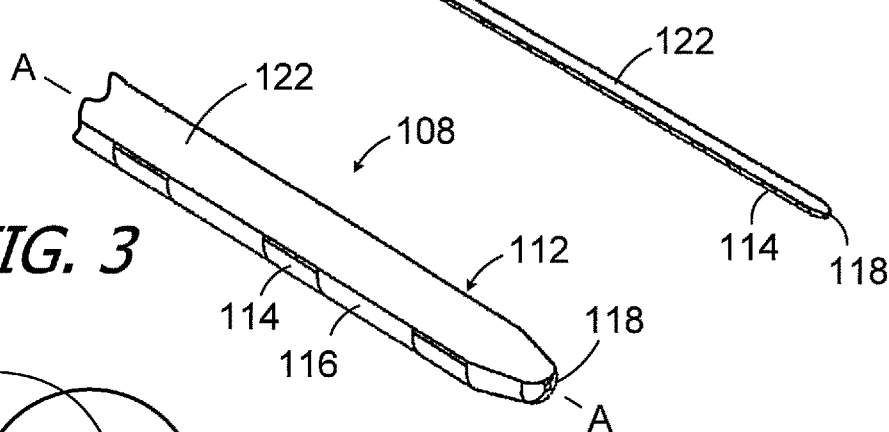
FIG. 2
FIG. 3
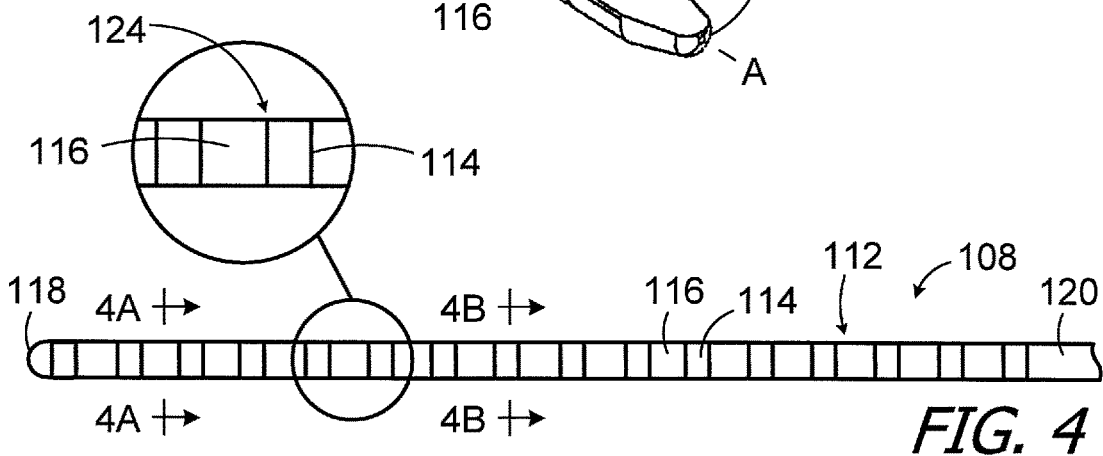
FIG. 4
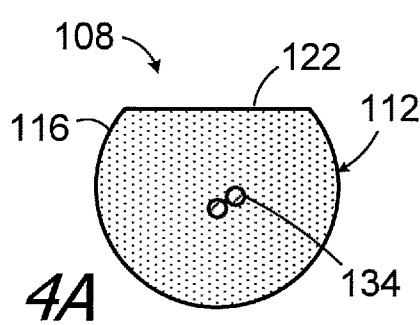
FIG. 4A
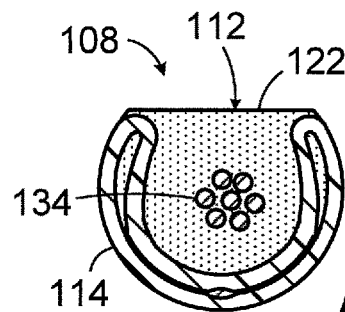
FIG. 4B

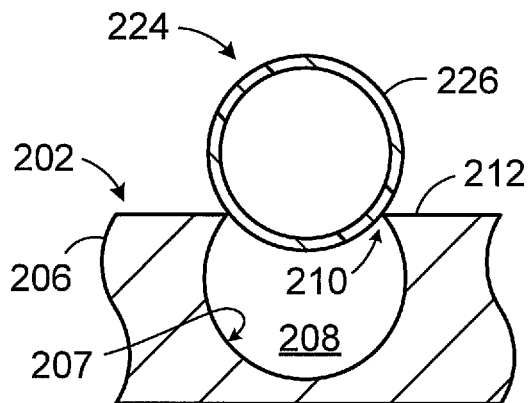
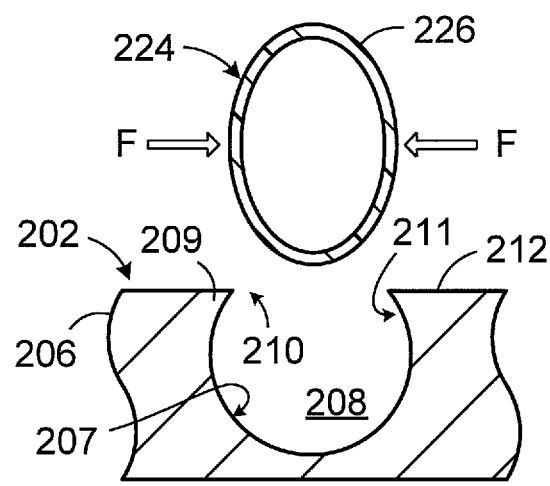
FIG. 7
FIG. 7A
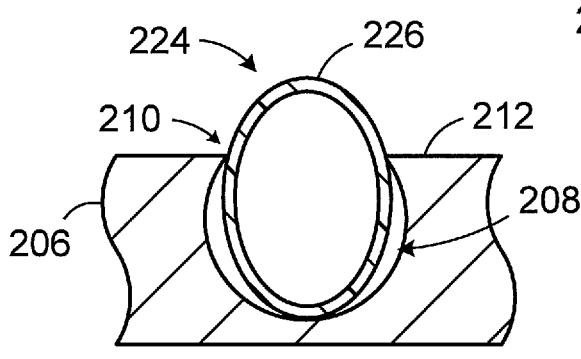
FIG. 7B
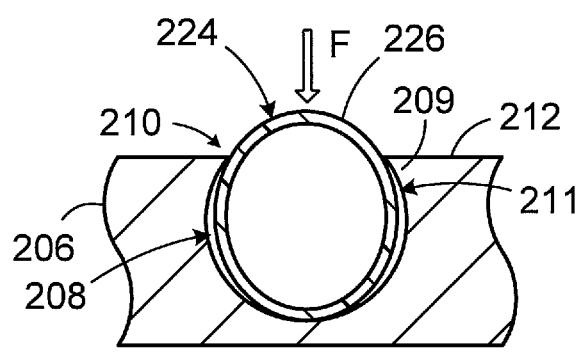
FIG. 7C
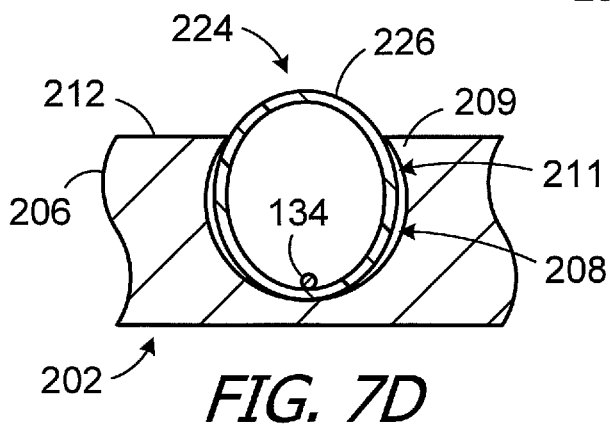
FIG. 7D

COCHLEAR IMPLANTS INCLUDING ELECTRODE ARRAYS AND METHODS OF MAKING THE SAME

CROSS-REFERENCE TO RELATED APPLICATIONS

This application is the U.S. National Stage of PCT App. Ser. No. PCT/US2016/046621, filed Aug. 11, 2016.

BACKGROUND

1. Field

The present disclosure relates generally to the implantable portion of implantable cochlear stimulation (or "ICS") systems and, in particular, to electrode arrays.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant") having a lead with an electrode array, a sound processor unit (e.g., a body worn processor or behind-the-ear processor) that communicates with the cochlear implant, and a microphone that is part of, or is in communication with, the sound processor unit. The cochlear implant electrode array, which is formed by a molding process, includes a flexible body formed from a resilient material such as liquid silicone rubber ("LSR") and a plurality of electrically conductive contacts (e.g., sixteen platinum contacts) spaced along a surface of the flexible body. The contacts of the array are connected to lead wires that extend through the flexible body. Once implanted, the contacts face the modiolus within the cochlea.

The present inventors have determined that conventional methods of manufacturing electrode arrays are susceptive to improvement. The electrically conductive contacts, which must have a clean exposed surface to function properly, are masked during the molding process to prevent the LSR or other resilient material from covering the contacts. In some conventional processes, the contacts are welded to an iron strip and connected to the lead wires. The iron strip masks portions of the contacts. The contacts, iron strip and lead wires are then placed into a mold that is configured to accommodate the iron strip. Resilient material is injected into the mold to form the flexible body of the electrode array through an overmolding process. The electrode array is removed from the mold once the resilient material has cured. The iron strip is then etched away from the contacts, in a bath of nitric acid or hydrochloric acid, thereby exposing the contacts. The contacts must be cleaned after the acid bath. The acid bath and cleaning take approximately 8 hours. The present inventors have determined that it would be desirable to avoid the use of harsh chemicals and the production delay associated therewith. The present inventors have also determined that welded masks can result in an uneven and uncontrolled contact surface, with small granulations in surface structure, which is more likely to experience biofilm and fibrous tissue growth than a smooth surface. Irregular surfaces are also likely to result in electrical impedances that vary from contact to contact.

SUMMARY

A method in accordance with one of the present inventions includes the steps of positioning a workpiece on a mold part such that a portion of the workpiece is within a channel of the mold part, compressing the workpiece to form a contact, and introducing resilient material into the channel to form a flexible body. There are a number of advantages associated with such a method. For example, the surface of the channel masks the outer surface of the contacts from the resilient material, thereby eliminating the need for welded masks and etching associated with some conventional methods. The present method also produces a smooth, clean surface that is less likely to experience biofilm and fibrous tissue grown after implantation or electrical impedances that vary from contact to contact.

A cochlear implant in accordance with one of the present inventions may have a housing, an antenna, a stimulation processor, and an electrode array, operably connected to the stimulation processor, including a flexible body defining a longitudinal axis and a truncated circle shape in a cross-section perpendicular to the longitudinal axis, and a plurality of electrically conductive contacts on the flexible body. There are a number of advantages associated with such an implant. For example, the truncated circle shape may have a flat surface that is positioned against the lateral wall during insertion of the electrode array into the cochlea, thereby preventing twisting of the electrode array.

A method in accordance with one of the present inventions comprises inserting an electrode array, including a flexible body, defining a longitudinal axis and a truncated circle shape with a flat surface in a cross-section perpendicular to the longitudinal axis, and a plurality of electrically conductive contacts on the flexible body, into a cochlea with a lateral wall in such a manner that at least a portion of the flat surface engages the lateral wall during insertion.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a cochlear implant in accordance with one embodiment of a present invention.

FIG. 2 is a perspective view of a portion of the cochlear lead illustrated in FIG. 1.

FIG. 3 is a perspective view of a portion of the cochlear lead illustrated in FIG. 1.

FIG. 4 is a bottom view of a portion of the cochlear lead illustrated in FIG. 1.

FIG. 4A is a section view taken along line 4A-4A in FIG. 4.

FIG. 4B is a section view taken along line 4B-4B in FIG. 4.

FIG. 7 a section view taken along line 7-7 in FIG. 6.

FIG. 7A is a section view of a portion of a molding process in accordance with one embodiment of a present invention.

FIG. 7B is a section view of a portion of a molding process in accordance with one embodiment of a present invention.

FIG. 7C is a section view of a portion of a molding process in accordance with one embodiment of a present invention.

FIG. 7D is a section view of a portion of a molding process in accordance with one embodiment of a present invention.

DETAILED DESCRIPTION OF THE EXEMPLARY EMBODIMENTS

Figure 5:
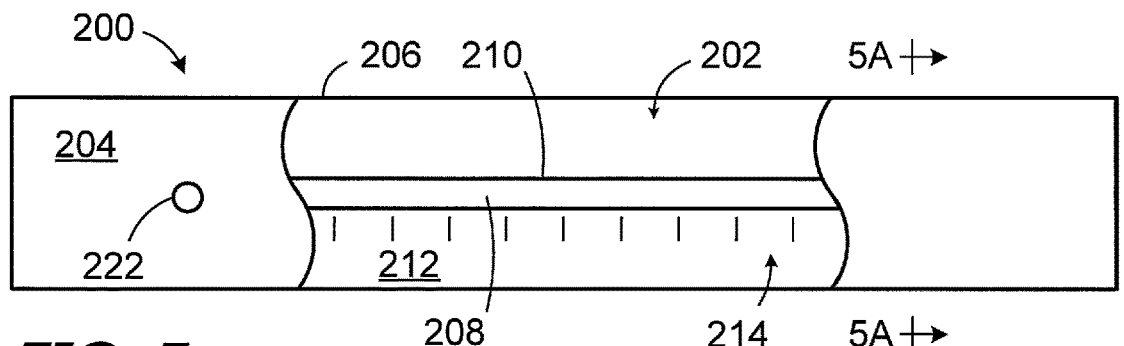
FIG. 5 is a plan view of a mold in accordance with one embodiment of a present invention.

The following is a detailed description of the best presently known modes of carrying out the inventions. This description is not to be taken in a limiting sense, but is made merely for the purpose of illustrating the general principles of the inventions.

One example of a cochlear implant (or "implantable cochlear stimulator") in accordance with at least some of the present inventions is illustrated in FIGS. 1-4B. The cochlear implant 100 includes a flexible housing 102 formed from a silicone elastomer or other suitable material, a processor assembly 104, a cochlear lead 106 with an electrode array 108, and an antenna 110 that may be used to receive data and power by way of an external antenna that is associated with, for example, a sound processor unit. The electrode array 108 includes a flexible body 112 and a plurality of electrically conductive contacts 114 (e.g., the sixteen contacts 114 illustrated in FIG. 4) spaced along the curved surface 116 of the flexible body. Suitable materials for the flexible body 112 include, but are not limited to, LSR, high temperature vulcanization ("HTV") silicone rubbers, room temperature vulcanization ("RTV") silicone rubbers, and thermoplastic elastomers ("TPEs"), while suitable materials for the contacts 114 include, but are not limited to, platinum, platinum-iridium, gold and palladium. The contacts 114 may be referred to in numbered order, $1^{st}$ through $16^{th}$, with the contact closest to the tip 118 being the $1^{st}$ contact and the contact closest to the base 120 being the $16^{th}$ contact. The exemplary flexible body 112 also includes a longitudinally extending planar (or "flat") surface 122 that does not include conductive contacts. Once implanted, the conductive contacts 114 on the curved surface 116 face the modiolus within the cochlea. The flat surface 122 reduces the likelihood that the electrode array 108 will rotate after being inserted into the cochlea, as is discussed below with reference to FIG. 23. It should also be noted that the methods of forming the electrode array described below produce smooth exterior surface transitions 124 from the flexible body 112 to the contacts 114.

Turning to FIG. 2, in addition to the electrode array 108, the exemplary cochlear lead 106 includes a wing 126, with a rectangular portion 128 and a tapered portion 130, which functions as a handle for the surgeon during the implantation surgery. The wing 126 also provides tension relief for the lead wires 134, which do not run straight through the wing. A tubular member 132, which may consist of tubes of different sizes, extends from the wing 126 to the housing 102. The contacts 114 are connected to lead wires 134 (FIG. 4A) that extend through the flexible body 112 and tubular member 132 to a connector (not shown) in the housing 102.

A positioning magnet 136 (FIG. 1) is located within a magnet pocket 138. The magnet 136 is used to maintain the position of a headpiece transmitter over the antenna 110. The cochlear implant may, in some instances, be configured is manner that facilitates magnet removal and replacement. Here, the housing 102 may be provided with a magnet aperture (not shown) that extends from the magnet pocket 138 to the exterior of the housing.

Referring to FIGS. 4A and 4B, the electrode array 108 has a truncated circle shape in a cross-section perpendicular to the longitudinal axis A (FIG. 3) of the electrode array. The circular portion of the perimeter of the cross-section, as defined by both the outer surface of the contacts 114 and the curved surface 116 of the flexible body 112, is more than one-half of the perimeter of the cross-section. Put another way, the contacts 114 and curved surface 116 extend more than 180 degrees around the longitudinal axis A of the electrode array 108. In other implementations, the contacts 114 and curved surface 116 may extend 130-180 degrees around the longitudinal axis A. It should also be noted here that the present contacts have a larger exposed area than conventional contacts, which results in lower impedance and longer battery life. The length of the flat surface 122 is less than the diameter of the truncated circle in the embodiment illustrated in FIGS. 1-4B.

Figure 5A:
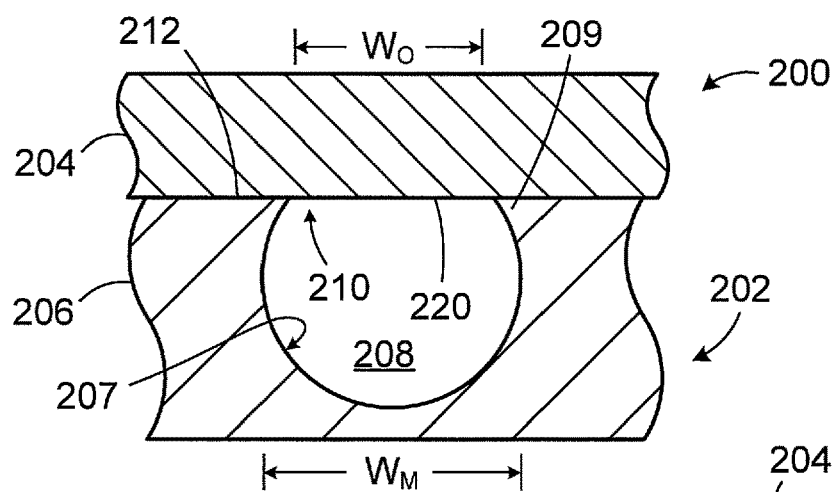
FIG. 5A is a section view taken along line 5A-5A in FIG. 5.
Figure 5B:
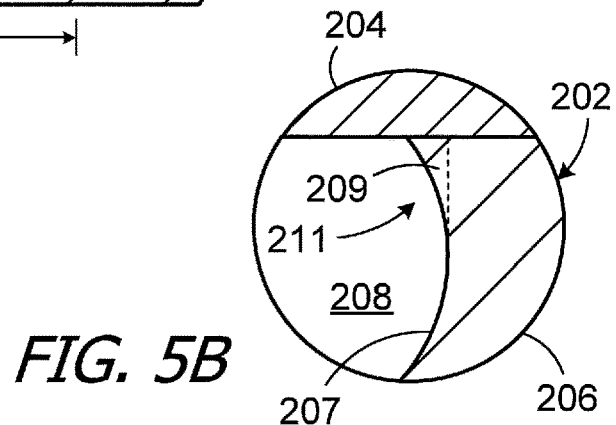
FIG. 5B is an enlarged view of a portion of FIG. 5A.

One exemplary method of forming an electrode array, such as the electrode array 108 illustrated in FIGS. 1-4B, may involve the use of the exemplary mold 200 illustrated in FIGS. 5 and 5A. Mold 200 has first and second mold parts 202 and 204. The first mold part 202 includes a plate 206 with a surface 207 that defines an elongate cavity 208 in the shape of the electrode array 108. Given the shape of the electrode array 108, the elongate cavity 208 has a truncated circle shape in a cross-section perpendicular to the longitudinal axis of the cavity. An opening 210 extends through the top surface 212 of the plate 206. The opening 210 has a width $W_o$ that is less than the maximum width $M_w$ of the elongate cavity 208 and, as a result, the first mold part 202 includes a pair of inwardly extending projections 209 that define undercuts 211 (FIG. 5B).

Figure 6:
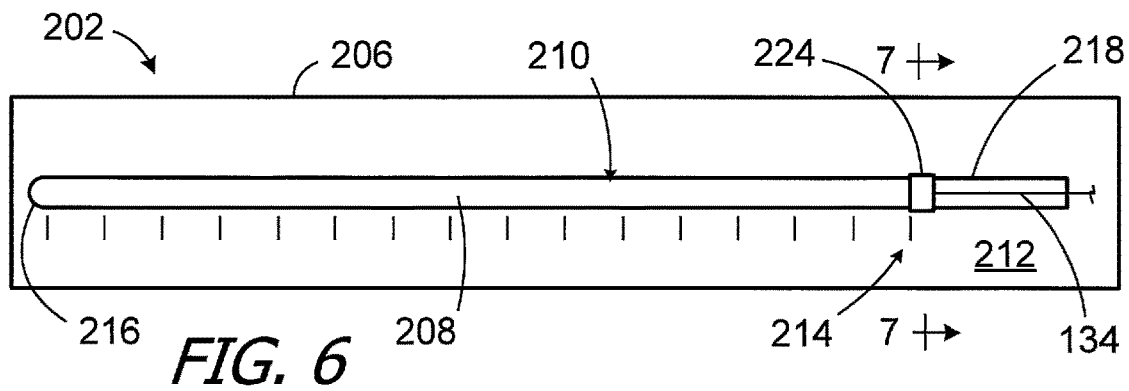
FIG. 6 is a plan view of a portion of a molding process in accordance with one embodiment of a present invention.

The top surface 212 of the exemplary first mold part 202 also includes markers 214 that correspond to the intended locations of the contacts 114 before and during the process that is described below with reference to FIGS. 6-17. Here, there is a single marker 214 for each of the contacts 114. In another implementation (not shown), a set of four markers 214 (two on each side of the cavity 208) may be provided for each of the contacts 114. The marker sets extend from the tip portion 216 of the cavity 208 to the base portion 218 of the cavity (FIG. 6). The second mold part 204, which includes a flat bottom surface 220 that faces the top surface 212 (and opening 210) of the first mold part 202, will be positioned over the first mold part after the contacts 114 have been positioned within the cavity 208 in the manner described below. The flat surface 220 shapes the flat surface 122 of the exemplary flexible body 112. The second mold part 204 also includes one or more inlets 222 for the injected LSR (or other resilient material) that forms the flexible body 112.

The first mold part 202 may in some instances be a disposable part formed by a photoetching process. Although iron and other photoetchable materials may be employed, the exemplary first mold part 202 is formed from copper, which is relatively inexpensive and has a number of advantageous properties. Copper is unlikely to bond to platinum contacts 114 because copper does not weld easily and has relatively high thermal conductivity, which causes heat to dissipate very readily. Copper is also resilient in that it will flex slightly and return to its shape when the platinum contact workpieces (discussed below) are pressed through the opening. Copper is easy to bend, which facilitates release of the electrode array (discussed below). Also, as copper is electrically conductive, it may be used in an opposed weld process where the copper mold part 202 forms part of the electrical loop. In other implementations, the mold part 202 may be a reusable apparatus that consists of two separable pieces formed from a harder material such as stainless steel. The second mold part 204 may be reusable and formed from stainless steel or any other suitable hard metal.

It should also be noted that the wing 126 (FIG. 2) may be formed with a stainless steel mold (not shown) which has a wing-shaped cavity and is aligned with the mold 200 during the injection process.

Turning to FIGS. 6-7D, the exemplary method includes placing a contact workpiece 224 onto the first mold part 202 at the location defined by the marker 214 closest to the base portion 218. Referring first to FIGS. 6 and 7, the exemplary contact workpiece 224 is a tube defined by a wall 226 formed from platinum or other suitable contact material. Although not limited to any particular shape, the exemplary workpiece is a cylindrical tube and is circular in cross-section. The diameter of the contact workpiece 224 is greater that the width $W_o$, (FIG. 5A) of the opening 210 and, as a result, the contact workpiece will not pass completely through the opening prior to being compressed in the manner described below. In the illustrated implementation, the diameter of the contact workpiece 224 is equal to the diameter of the cavity 208.

Turning to FIG. 7A, the contact workpiece 224 may be compressed with a tweezers or other suitable instrumentality into a non-circular (e.g., elliptical) shape by applying force F to the lateral sides of the wall 226 until the width of the contact workpiece is slightly less than, equal to, or no more than slightly greater than, the width $W_o$, of the opening 210. The compressed contact workpiece 224 may then be inserted through the opening 210 and into the cavity 208 (FIG. 7B). The resilience of the mold part 202 will allow the opening to widen slightly in those instances where the width of the compressed contact workpiece 224 is slightly greater than the width $W_o$, of the opening 210. Force F may then be applied to the top of the compressed contact workpiece 224, in the manner illustrated in FIG. 7C, to cause the contact workpiece bulge outwardly into the original circular cross-sectional shape or a shape close to the original circular cross-sectional shape (as shown). Here, portions of the contact workpiece 224 are located under the projections 209 and within the undercuts 211. The lead wire 134 that will be connected to the contact 114 formed by the workpiece 224 may then be positioned within the workpiece, as shown in FIG. 7D. The portion of the lead wire 134 within the workpiece 224 may be stripped of insulation prior to the being inserted into the workpiece, or the insulation may simply be allowed to burn off during the application of heat and pressure to the workpiece (described below with reference to FIG. 8).

Figure 8:
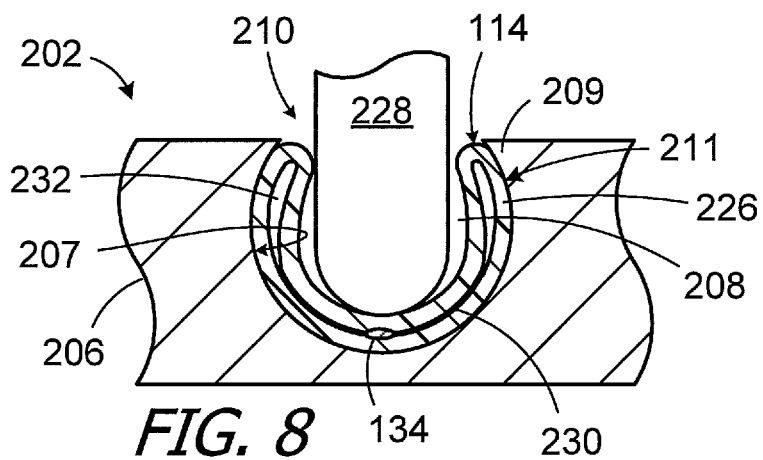
FIG. 8 is a partial section view of a portion of a molding process in accordance with one embodiment of a present invention.
Figure 9:
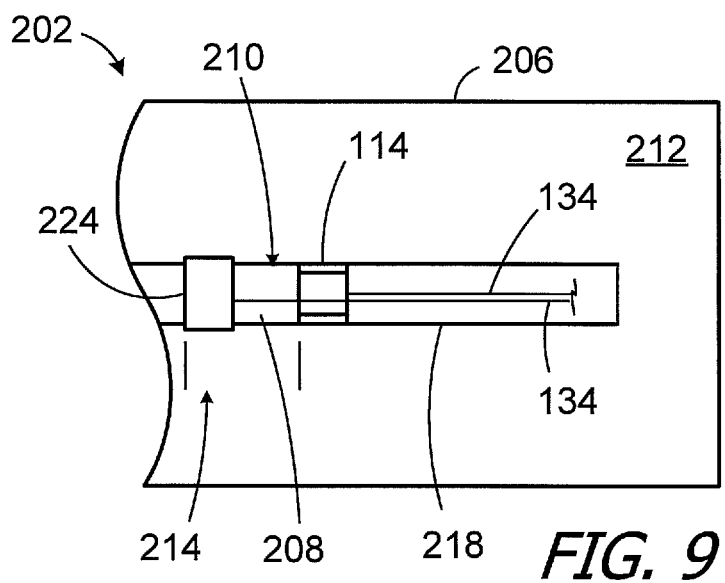
FIG. 9 is a plan view of a portion of a molding process in accordance with one embodiment of a present invention.

Next, as illustrated in FIG. 8, heat and pressure are applied to the contact workpiece to form the contact 114. The contact 114 is pressed tightly against the mold surface 207 that defines the cavity 208, thereby preventing movement of the contact. The surface 207 masks the outer surface of the contact 114 and defines the outer surface of flexible body 112 in the spaces not covered by the contacts 114. Portions of the contact 114 are located under the projections 209 and within the undercuts 211. The compression and distortion of the malleable workpiece 224 also cause portions of the wall 226 to come into contact with one another along a seam 230 with the lead wire 134 therebetween. In some but not all instances, and as is the case in the illustrated implementation, gaps 232 may be formed between other portions of the wall 226. The gaps 232 augment the mechanical interconnection between the flexible body 112 and the contacts 114, as is discussed below with reference to FIG. 16.

Figure 10:
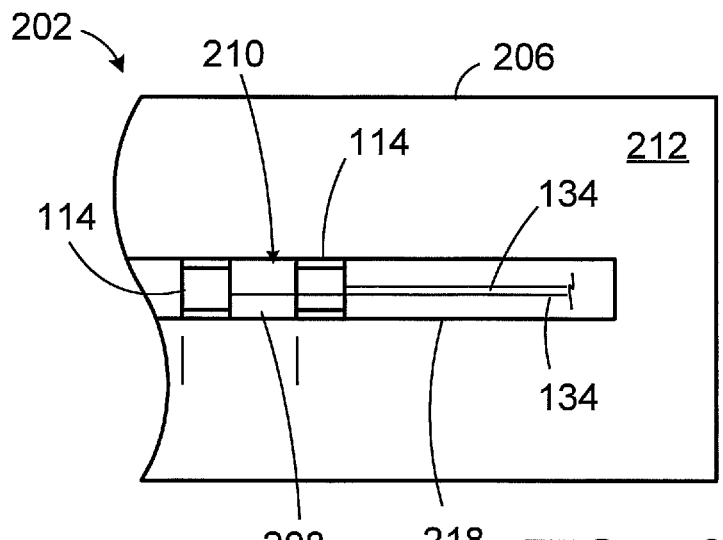
FIG. 10 is a plan view of a portion of a molding process in accordance with one embodiment of a present invention.
Figure 11:
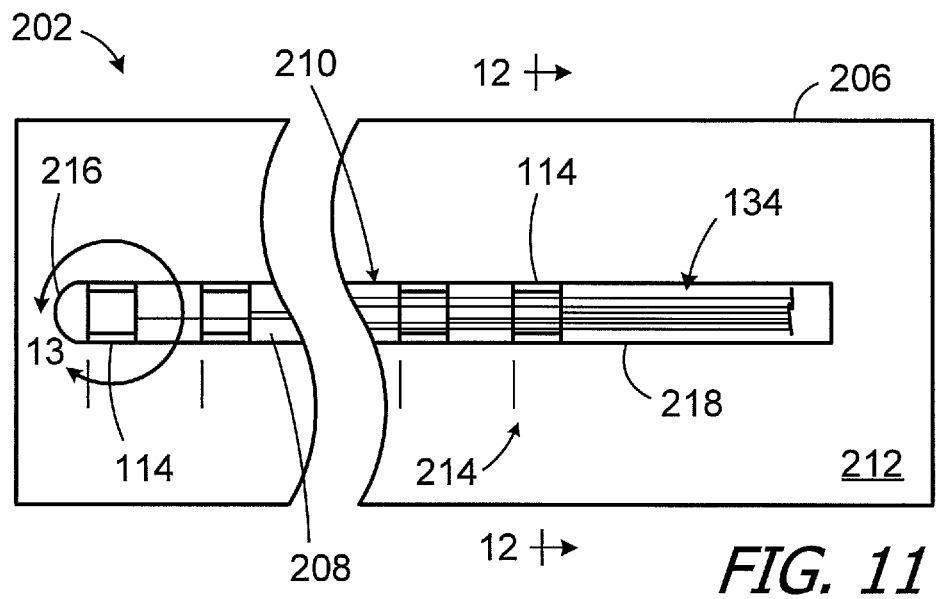
FIG. 11 is a plan view of a portion of a molding process in accordance with one embodiment of a present invention.
Figure 12:
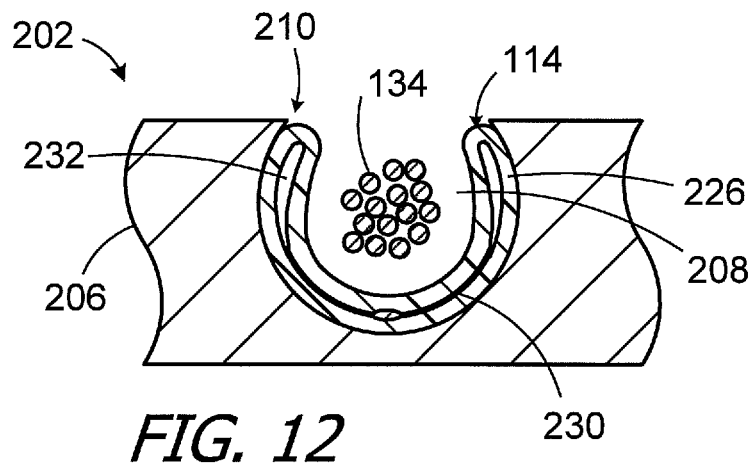
FIG. 12 a section view taken along line 12-12 in FIG. 11.
Figure 13:
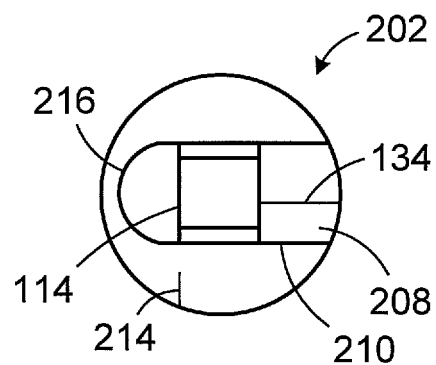
FIG. 13 is an enlarged view of a portion of FIG. 11.

The steps illustrated in FIGS. 6-8 may then be repeated to form the remainder to the contacts 114. To that end, and referring to FIG. 9, the next contact workpiece 224 may be placed onto the first mold part 202 at the location defined by the next adjacent marker 214 in the manner described above with reference to FIGS. 7-7D. The lead wire 134 that will be connected to the contact 114 formed by this workpiece 224 is positioned within workpiece and extends over the previously prepared contact to and beyond the base portion 218 of the cavity 208. Heat and pressure are then applied to the workpiece 224 with, for example, a weld tip, such as the molybdenum weld tip 228 in a resistance welding process. The heat and pressure compress the workpiece 224 against the surface 207 that defines the cavity 208, thereby forming the second contact 114 (FIG. 10). This process is repeated until the last contact 114 is formed in the region adjacent to the tip portion 216 of the cavity 208, as is illustrated in FIGS. 11-13.

In other implementations, the contacts 114 may be formed by compressing the workpiece 224 with a stainless steel weld tip (no heat applied) and then applying heat with a molybdenum weld tip, thereby preventing wear on both weld tips.

Figure 14:
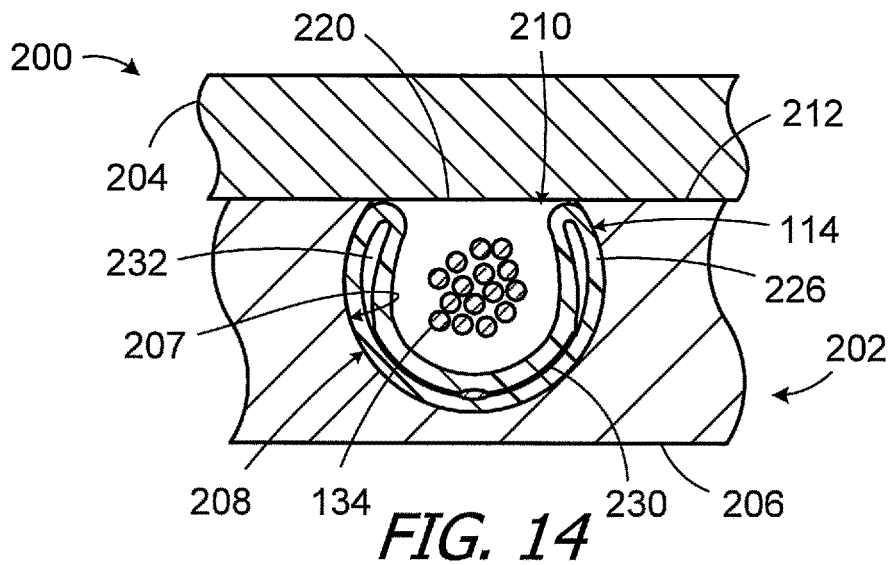
FIG. 14 is a section view of a portion of a molding process in accordance with one embodiment of a present invention.
Figure 15:
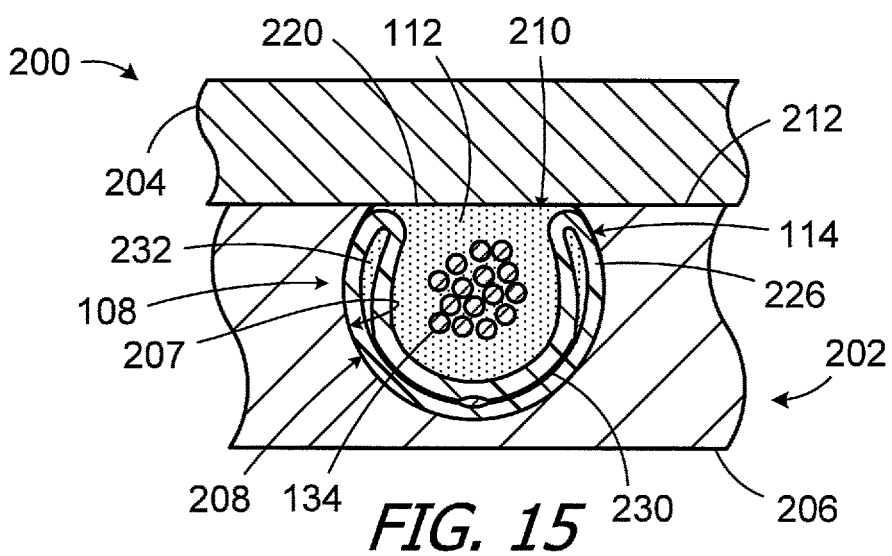
FIG. 15 is a section view of a portion of a molding process in accordance with one embodiment of a present invention.
Figure 15A:
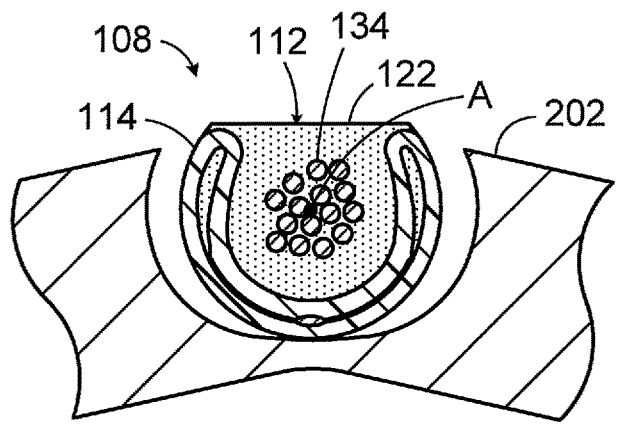
FIG. 15A is a section view of a portion of a molding process in accordance with one embodiment of a present invention.

Once all of the contacts 114 have been formed and connected to respective lead wires 134, the second mold part 204 may be placed over the first mold part 202 to complete the mold 200 in the manner illustrated in FIGS. 14 and 15. A clamp, screws or other suitable instrumentality (not shown) may be used to hold the mold parts 202 and 204 together. The LSR or other suitable resilient material may then be injected (or otherwise introduced) into the mold cavity 208 to form the flexible body 112. The masking effect of the mold surface 207 prevents the resilient material from flashing over the outer surfaces of the contacts 114. After the resilient material hardens, the mold parts 202 and 204 may be separated from one another. The completed electrode array 108 may be removed from the cavity 208 by, for example, bending the mold part 202 so as to increase the width $W_o$ of the opening 210 in the manner illustrated in FIG. 15A. The bent and/or broken mold part 202 may then be disposed of.

Figure 16:
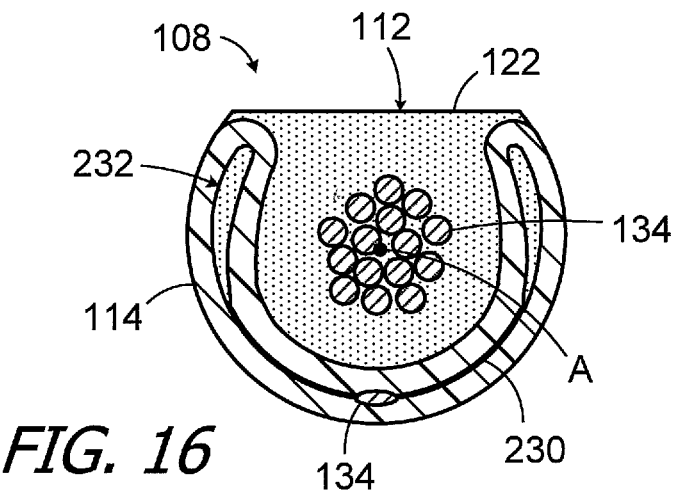
FIG. 16 is a section view of an electrode assembly in accordance with one embodiment of a present invention.

Turning to FIG. 16, the now-completed electrode array 108 includes the aforementioned flexible body 112, contacts 114 and lead wires 134. The flat surface 122 of the flexible body 112 does not include contacts 114 or other conductive elements. The contracts 114 extend more than 180 degrees around the longitudinal axis A in the illustrated embodiment. In other embodiments, the contacts may extend 180 degrees or less around the longitudinal axis A. The outer surfaces of the contacts 114 are free of resilient material due to the masking effect of surface 207. The lead wires 134 are each connected to a respective one of the contacts and pass through the open central region defined by the other contacts. Portions of the flexible body 112 are located with the contact gaps 232, thereby augmenting the mechanical interconnection between the flexible body 112 and the contacts 114.

Figure 17:
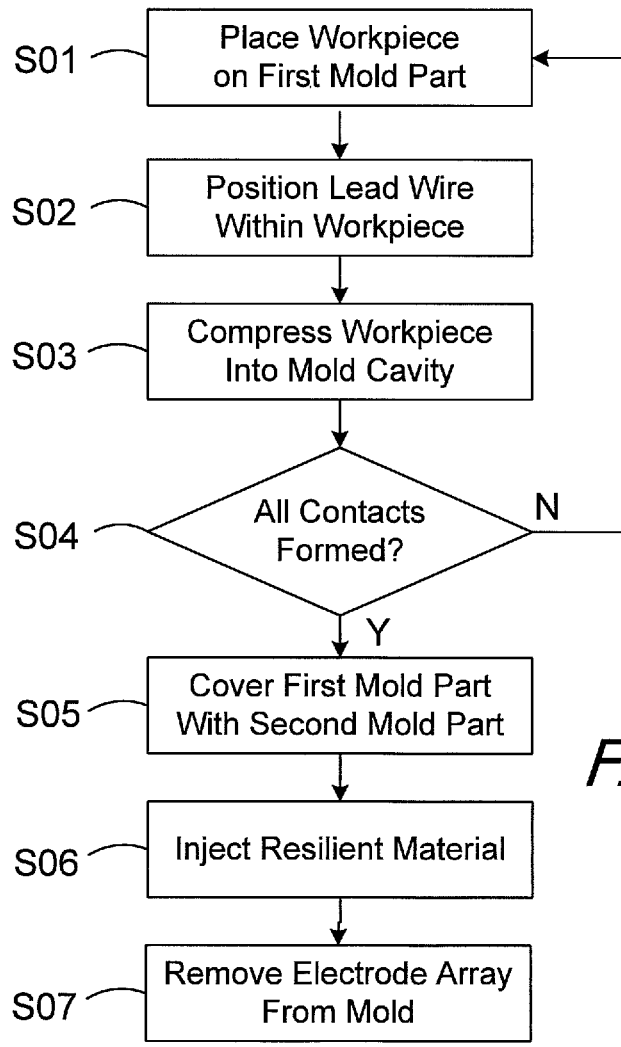
FIG. 17 is a flow chart showing a method in accordance with one embodiment of a present invention.

The various method steps described above are summarized in the flow chart illustrated in FIG. 17. The first workpiece 224 is positioned in the intended location within the first mold part 202, as is identified by the indicia 214, adjacent to the base portion 218 of the cavity 208 (Step S01). A lead wire 134 is placed within the workpiece 224 (Step S02). It should be noted here that the order of steps S01 and S02 may be reversed, or steps S01 and S02 may be performed simultaneously. The workpiece 224 is then compressed through the use of, for example, heat and pressure applied by the weld tip 228, to form a contact 114 (Step S03). This process is repeated until all of the contacts 114 have been formed within the mold cavity 208 (Step S04). Once all of the contacts 114 have been formed, the second mold part 204 may be placed over the first mold part 202 (Step S05) and LSR or other resilient material may be injected into the mold cavity 208 (Step S06). The completed electrode array 108 may be removed from the first mold part 202 after the resilient material has cured (Step S07).

The present apparatus and methods are not limited to the exemplary implementation described above. In other implementations of the present method, all of the workpieces 224 may be positioned within the cavity 208 of the first mold part 202 without the lead wires 134. Thereafter, and beginning with the workpiece 224 closest to the base portion 218 of the cavity 208, a lead wire 134 may be inserted into a workpiece and that workpiece may be compressed (e.g., with heat and pressure applied by a weld tip) to form a contact 114. This process may be repeated until the last contact 114 has been formed within the cavity 208. LSR or other resilient material may then be injected into the mold cavity 208 in the manner described above to complete the electrode array 108.

Figure 18:
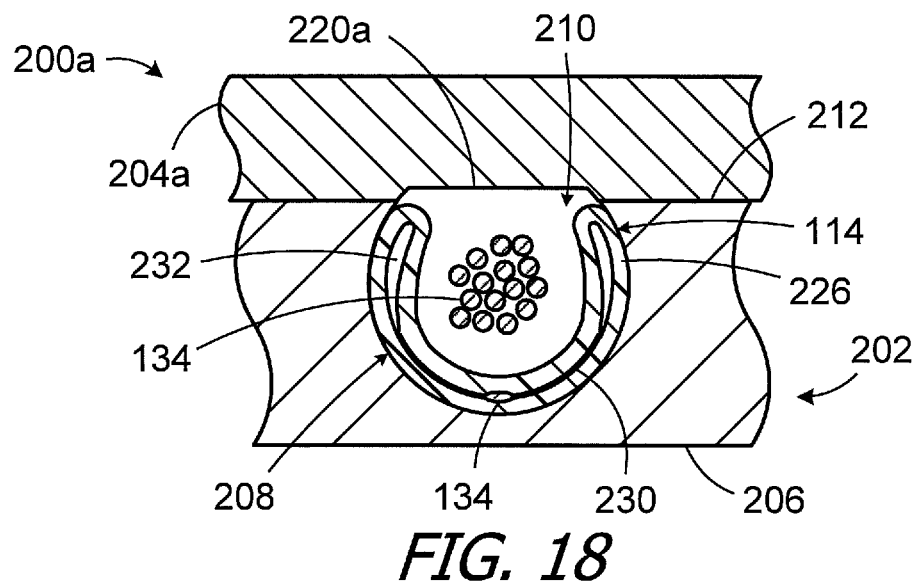
FIG. 18 is a section view of a portion of a molding process in accordance with one embodiment of a present invention.
Figure 19:
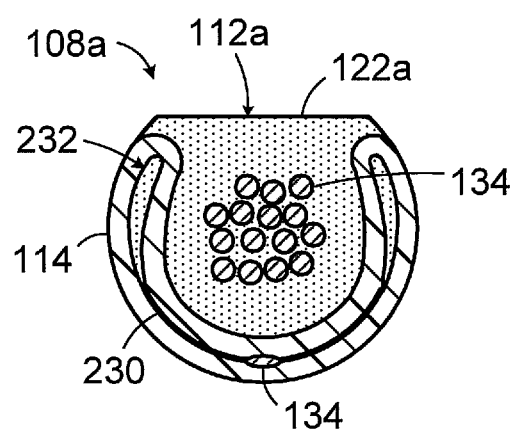
FIG. 19 is a section view of an electrode assembly in accordance with one embodiment of a present invention.

The present methods may also be used to form other electrode arrays with flat surfaces, as well as arrays with curved or otherwise non-flat surfaces. By way of example, but not limitation, the exemplary mold 200a illustrated in FIG. 18 is substantially similar to mold 200 and similar elements are represented by similar reference numerals. Here, however, the second mold part 204a includes a recess 220a that is aligned with the opening 210 of the first mold part 202. The electrode array 108a (FIG. 19) produced by the mold 200a is substantially similar to the electrode array 108 and similar elements are represented by similar reference numerals. Here, however, the flexible body 112a has a flat surface 122a that is a greater distance from the contacts 114 than is the flat surface 122 of flexible body 112 (FIG. 16).

Figure 20:
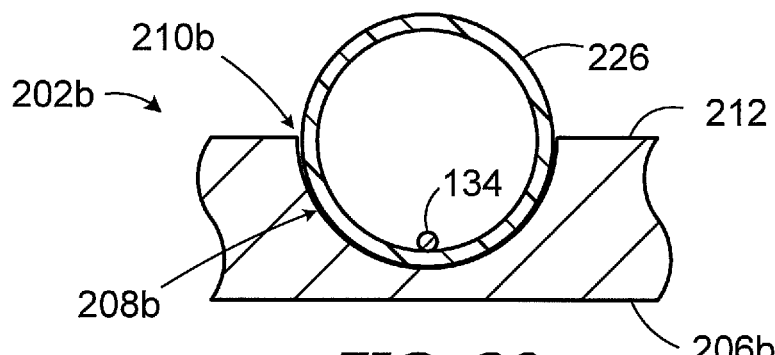
FIG. 20 is a section view of a portion of a molding process in accordance with one embodiment of a present invention.
Figure 21:
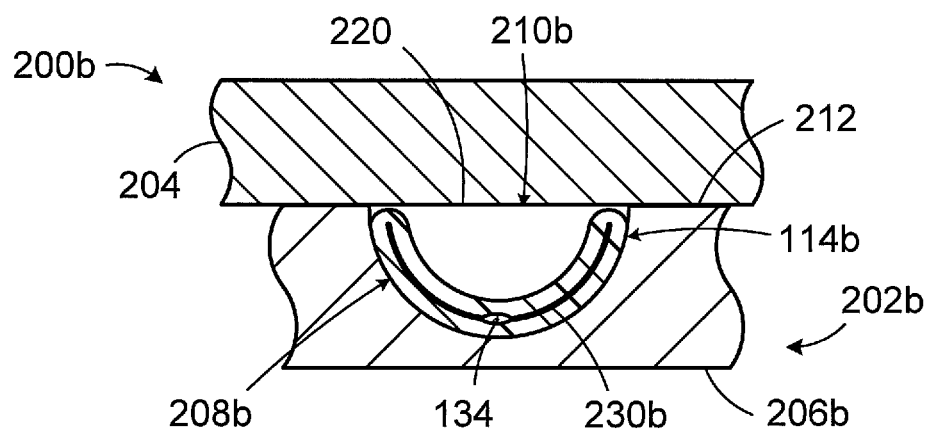
FIG. 21 is a section view of a portion of a molding process in accordance with one embodiment of a present invention.
Figure 22:
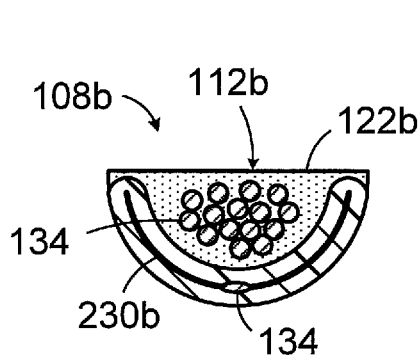
FIG. 22 is a section view of an electrode assembly in accordance with one embodiment of a present invention.

Turning to FIGS. 20 and 21, the exemplary mold 200b is substantially similar to mold 200 and similar elements are represented by similar reference numerals. Here, however, the first mold part 202b includes a plate 206b with an elongate cavity 208b is semi-circular (i.e., 180 degrees) in a cross-section perpendicular to the longitudinal axis of the cavity. An opening 210b extends through the top surface 212 of the plate 206b. The width of the opening 210b is equal to the diameter of the workpiece 224. As a result, the workpiece 224 passes through the opening 210b, and into the cavity 208b when the workpiece is placed onto the first mold part 202b, without the compression described above with reference to FIGS. 7-7D. The workpiece 224 may be compressed (e.g., by heat and pressure applied by a weld tip) to form a semi-circular contact 114b, with a seam 230b, that is connected to a lead wire 134. Once all of the contacts 114b have been formed and connected to respective lead wires 134, the second mold part 204 may be placed over the first mold part 202b to complete the mold 200b. The LSR or other suitable resilient material may then be injected into the mold cavity 208b to form the flexible body 112b of the electrode array 108b illustrated in FIG. 22. The electrode array 108b is substantially similar to the electrode array 108 and similar elements are represented by similar reference numerals. Here, however, the flexible body 112a has a flat surface 122a with a width that is equal to the diameter of the semi-circular electrode array 108b, which allows the electrode array 108b to be removed from the mold part 202b without bending and/or destroying the mold part.

Figure 23:
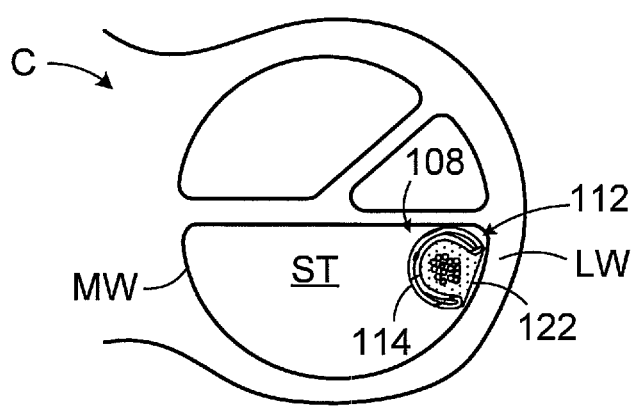
FIG. 23 is a section view of the electrode assembly illustrated in FIGS. 1-4B positioned within a cochlea.

As illustrated for example in FIG. 23, the exemplary electrode array 108 may be positioned within the scala tympani ST of the cochlea C in such a manner that the flat surface 122 of the flexible body 112 is facing the lateral wall LW and the contacts 114 are facing the medial wall MW. Some or all of the flat surface 122 is positioned against the lateral wall during insertion of the electrode array 108 into the cochlea, thereby reducing the likelihood that the electrode array will twist. Preferably, the flat surface 122 remains against the lateral surface LW for the entire insertion process, i.e. from the entry of the tip 118 into the cochlea by way of the round window (or a cochleostomy), to the point at which the portion of the electrode array 108 with the contacts 114 has passed through the round window (or cochleostomy) and is within the cochlea. The contacts 114 and the curved surface 116 of the flexible body 112 face the modiolus within the cochlea and the medial wall MW during (as well as after) insertion.

Figure 24:
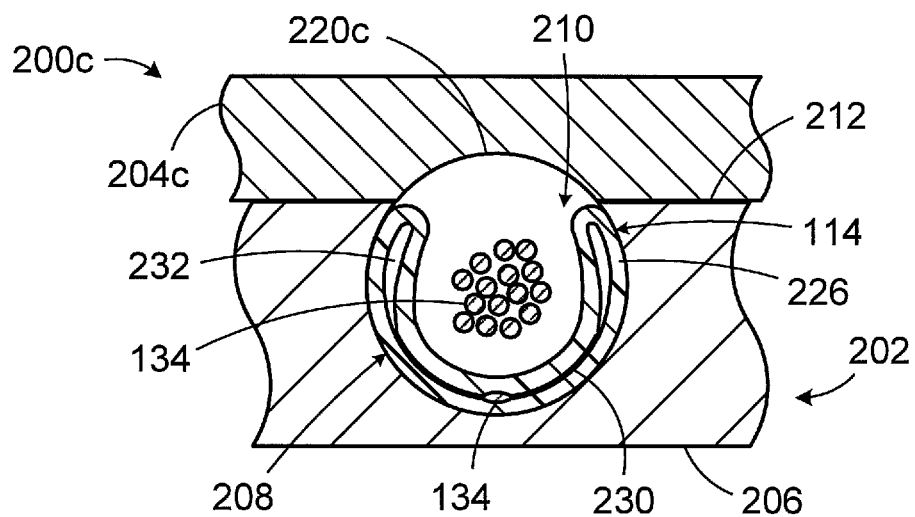
FIG. 24 is a section view of a portion of a molding process in accordance with one embodiment of a present invention.
Figure 25:
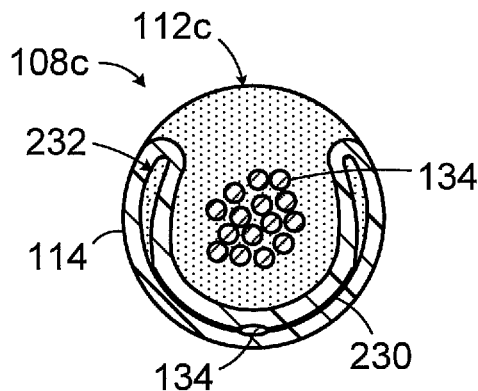
FIG. 25 is a section view of an electrode assembly in accordance with one embodiment of a present invention.
Figure 26:
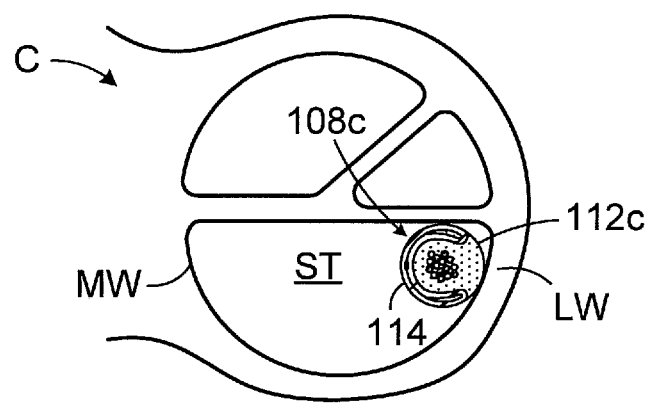
FIG. 26 is a section view of the electrode assembly illustrated in FIGS. 24 and 25 positioned within a cochlea.

It should be noted that the present apparatus and methods are not limited to electrode arrays with a flat surface. To that end, and referring to FIG. 24, the exemplary mold 200c is substantially similar to mold 200 and similar elements are represented by similar reference numerals. Here, however, the second mold part 204c includes a recess 220c that is aligned with the opening 210 of the first mold part 202. The recess 220c has a radius of curvature that is equal to that of the recess 208. Thus, when combined, the recess 208 and the recess 220c define a circle in a plane perpendicular to the longitudinal axis of the recess 208. The electrode array 108c (FIG. 25) produced by the mold 200c is substantially similar to the electrode array 108 and similar elements are represented by similar reference numerals. Here, however, the electrode array 108c defined by the flexible body 112c and the contacts 114 is circular in cross-section. The exemplary electrode array 108c may be positioned within the scala tympani ST of the cochlea C in the manner illustrated in FIG. 26.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:
a housing;
an antenna within the housing;
a stimulation processor within the housing operably connected to the antenna; and
an electrode array, operably connected to the stimulation processor, including a flexible body defining a longitudinal axis and a truncated circle shape in a cross-section perpendicular to the longitudinal axis, and a plurality of electrically conductive contacts on the flexible body that extend uninterruptedly more than 180 degrees around the longitudinal axis.

2. A cochlear implant as claimed in claim 1, wherein the flexible body includes a curved surface and a flat surface; and
the electrically conductive contacts are located on the curved surface of the flexible body and have a surface that defines a partial circle which extends uninterruptedly more than 180 degrees around the longitudinal axis.

3. A cochlear implant as claimed in claim 2, wherein there are no electrically conductive contacts on the flat surface.

4. A cochlear implant as claimed in claim 2, wherein the flexible body defines a diameter; and
the flat surface defines a width that is less than the diameter.

5. A cochlear implant as claimed in claim 2, wherein the flexible body defines a diameter; and
the flat surface defines a width that is equal to the diameter.

6. A cochlear implant as claimed in claim 1, wherein the electrode array is formed by a method comprising the steps of:
positioning a workpiece on a mold part with a channel having an undercut such that a portion of the workpiece is within the channel of the mold part;
compressing the workpiece to form a contact; and
introducing resilient material into the channel to form a flexible body.

7. A cochlear implant as claimed in claim 6, wherein the method further comprises the step of
positioning a lead wire within the workpiece prior to the step of compressing the workpiece.

8. A cochlear implant as claimed in claim 6, wherein the workpiece comprises a tubular workpiece.

9. A cochlear implant as claimed in claim 6, wherein wherein the mold part comprises a first mold part; and
the method further comprises the step of positioning a second mold part over the first mold part such that a flat surface of the second mold part covers the inlet.

10. A cochlear implant as claimed in claim 6, wherein the step of compressing the workpiece comprises applying heat and pressure to the workpiece.

11. A cochlear implant as claimed in claim 6, wherein the channel is defined by a surface of the mold part; and
the step of compressing the workpiece comprises compressing the workpiece against a portion of the mold part surface such that the portion of the mold part surface forms a mask over an outer surface of the contact that prevents the resilient material from covering the outer surface of the contact during the introducing step.

12. A cochlear implant, comprising:
a housing;
an antenna within the housing;
a stimulation processor within the housing operably connected to the antenna; and
an electrode array, operably connected to the stimulation processor, including
a flexible body defining a longitudinal axis and a truncated circle shape in a cross-section perpendicular to the longitudinal axis,
a plurality of lead wires extending through the flexible body, and
a plurality of electrically conductive contacts on the flexible body that each include first and second wall portions in contact with one another along a seam, which is arcuate in a plane perpendicular to the longitudinal axis, with a portion of one of the lead wires therebetween.

13. A cochlear implant as claimed in claim 12, wherein
the electrically conductive contacts include gaps between
the first and second wall portions adjacent to the seam;
and
portions of the flexible body are located within the gaps.

14. A cochlear implant as claimed in claim 12, wherein
the flexible body includes a curved surface and a flat
surface; and
the electrically conductive contacts are located on the
curved surface.

15. A cochlear implant as claimed in claim 14, wherein
there are no electrically conductive contacts on the flat
surface.

16. A cochlear implant as claimed in claim 15, wherein
the electrically conductive contacts extend more than 180
degrees around the longitudinal axis.

17. A cochlear implant as claimed in claim 14, wherein
the flexible body defines a diameter; and
the flat surface defines a width that is less than the
diameter.

18. A cochlear implant as claimed in claim 14, wherein
the flexible body defines a diameter; and
the flat surface defines a width that is equal to the
diameter.

19. A cochlear implant as claimed in claim 12, wherein
the first and second wall portions are both in contact with
the portion of the wire therebetween.

* * * * *